United States Patent
Mathivanan et al.

(10) Patent No.: US 10,942,987 B1
(45) Date of Patent: Mar. 9, 2021

(54) HEALTHCARE CLAIM DATA RECREATION FOR SUPPORT AND ANALYSIS

(71) Applicant: TriZetto Corporation, Denver, CO (US)

(72) Inventors: Sibi Mathivanan, Chandler, AZ (US); Aarti Vaswani, Phoenix, AZ (US)

(73) Assignee: Cognizant TriZetto Software Group, Inc., Englewood, CO (US)

(*) Notice: Subject to any disclaimer, the term of this patent is extended or adjusted under 35 U.S.C. 154(b) by 479 days.

(21) Appl. No.: 15/386,698

(22) Filed: Dec. 21, 2016

Related U.S. Application Data

(60) Provisional application No. 62/271,722, filed on Dec. 28, 2015.

(51) Int. Cl.
  *G06F 19/00* (2018.01)
  *G06F 16/28* (2019.01)
  *G06F 16/22* (2019.01)

(52) U.S. Cl.
  CPC ........ *G06F 19/328* (2013.01); *G06F 16/2228* (2019.01); *G06F 16/288* (2019.01)

(58) Field of Classification Search
  CPC combination set(s) only.
  See application file for complete search history.

(56) References Cited

U.S. PATENT DOCUMENTS

| | | | |
|---|---|---|---|
| 5,560,005 A | * | 9/1996 | Hoover et al. |
| 6,098,075 A | * | 8/2000 | Becraft, Jr. et al. |
| 6,604,110 B1 | * | 8/2003 | Savage et al. |
| 9,514,164 B1 | * | 12/2016 | Matic et al. |
| 2010/0246827 A1 | * | 9/2010 | Lauter et al. |
| 2011/0301982 A1 | * | 12/2011 | Green et al. |
| 2014/0136472 A1 | * | 5/2014 | Frafjord |
| 2014/0351409 A1 | * | 11/2014 | Basoglu et al. |
| 2015/0127687 A1 | * | 5/2015 | Graves |
| 2015/0142734 A1 | * | 5/2015 | Mueller |
| 2015/0187036 A1 | * | 7/2015 | Wang et al. |

(Continued)

FOREIGN PATENT DOCUMENTS

WO  WO 2013/174452  11/2013  ............. G06F 17/30

OTHER PUBLICATIONS

"Import and Export Data With the SQL Server Import and Export Wizard," Mar. 24, 2017, 3 pp., Retrieved from the Internet: https://opbuildstorageprod.blob.core.windows.net/output-pdf-files/en-us/SQL.sql-content/live/integration-services/import-export-data.pdf.

(Continued)

*Primary Examiner* — Michael Tomaszewski
*Assistant Examiner* — William T. Monticello
(74) *Attorney, Agent, or Firm* — Dawn-Marie Bey; Bey & Cotropia PLLC

(57) ABSTRACT

Enhanced methods for providing software support and resolving software support issues are provided, particularly those related to an entity, including a specific entity in a database. A method selects an entity, such as a healthcare claim or other entity in a database, for which there is a software issue. The method then identifies all data and relationships relevant to that entity, including all related tables and data for that entity. The specific entity, data, and relationships are then exported. This method provides better, more efficient, and enhanced software support by exporting not only the identified entity, but all other relevant data and relationships to that entity, for analysis in resolving any software support issues.

18 Claims, 13 Drawing Sheets

(56) References Cited

U.S. PATENT DOCUMENTS

2016/0048937 A1* 2/2016 Mathura et al.
2017/0052766 A1* 2/2017 Garipov

OTHER PUBLICATIONS

"Get Started With This Simple Example of the Import and Export Wizard," Mar. 27, 2017, 10 pp., Retrieved from the Internet: https://opbuildstorageprod.blob.core.windows.net/output-pdf-files/en-us/SQL.sql-content/live/integration-services/import-export-data.pdf.

"Start the SQL Server Import and Export Wizard," Mar. 24, 2017, 4 pp., Retrieved From the Internet: https://opbuildstorageprod.blob.core.windows.net/output-pdf-files/en-us/SQL.sql-content/live/integration-services/import-export-data.pdf.

"Connect to Data Sources With the SQL Server Import and Export Wizard," Mar. 24, 2017, 2 pp., Retrieved From the Internet: https://opbuildstorageprod.blob.core.windows.net/output-pdf-files/en-us/SQL.sql-content/live/integration-services/import-export-data.pdf.

"Connect to a SQL Server Data Source (SQL Server Import and Export Wizard)," Mar. 24, 2017, 5 pp., Retrieved From the Internet: https://opbuildstorageprod.blob.core.windows.net/output-pdf-files/en-us/SQL.sql-content/live/integration-services/import-export-data.pdf.

"Connect to an Oracle Data Source (SQL Server Import and Export Wizard)," Mar. 24, 2017, 5 pp., Retrieved From the Internet: https://opbuildstorageprod.blob.core.windows.net/output-pdf-files/en-us/SQL.sql-content/live/integration-services/import-export-data.pdf.

"Connect to a Flat File Data Source (SQL Server Import and Export Wizard)," Mar. 24, 2017, 14 pp., Retrieved From the Internet: https://opbuildstorageprod.blob.core.windows.net/output-pdf-files/en-us/SQL.sql-content/live/integration-services/import-export-data.pdf.

"Connect to an Excel Data Source (SQL Server Import and Export Wizard)," Mar. 27, 2017, 3 pp., Retrieved From the Internet: https://opbuildstorageprod.blob.core.windows.net/output-pdf-files/en-us/SQL.sql-content/live/integration-services/import-export-data.pdf.

"Connect to an Access Data Source (SQL Server Import and Export Wizard)," Mar. 27, 2017, 4 pp., Retrieved From the Internet: https://opbuildstorageprod.blob.core.windows.net/output-pdf-files/en-us/SQL.sql-content/live/integration-services/import-export-data.pdf.

"Connect to Azure Blob Storage (SQL Server Import and Export Wizard)," Mar. 24, 2017, 2 pp., Retrieved From the Internet: https://opbuildstorageprod.blob.core.windows.net/output-pdf-files/en-us/SQL.sql-content/live/integration-services/import-export-data.pdf.

"Connect to an ODBC Data Source (SQL Server Import and Export Wizard)," Mar. 24, 2017, 10 pp., Retrieved From the Internet: https://opbuildstorageprod.blob.core.windows.net/output-pdf-files/en-us/SQL.sql-content/live/integration-services/import-export-data.pdf.

"Connect to a PostgreSQL Data Source (SQL Server Import and Export Wizard)," Apr. 14, 2017, 4 pp., Retrieved From the Internet: https://opbuildstorageprod.blob.core.windows.net/output-pdf-files/en-us/SQL.sql-content/live/integration-services/import-export-data.pdf.

"Connect to a MySQL Data Source (SQL Server Import and Export Wizard)," Apr. 14, 2017, 4 pp., Retrieved From the Internet: https://opbuildstorageprod.blob.core.windows.net/output-pdf-files/en-us/SQL.sql-content/live/integration-services/import-export-data.pdf.

"Steps in the SQL Server Import and Export Wizard," Mar. 24, 2017, 2 pp., Retrieved From the Internet: https://opbuildstorageprod.blob.core.windows.net/output-pdf-files/en-us/SQL.sql-content/live/integration-services/import-export-data.pdf.

"Welcome to SQL Server Import and Export Wizard," Mar. 24, 2017, 2 pp., Retrieved From the Internet: https://opbuildstorageprod.blob.core.windows.net/output-pdf-files/en-us/SQL.sql-content/live/integration-services/import-export-data.pdf.

"Choose a Data Source (SQL Server Import and Export Wizard)," Mar. 24, 2017, 2 pp., Retrieved From the Internet: https://opbuildstorageprod.blob.core.windows.net/output-pdf-files/en-us/SQL.sql-content/live/integration-services/import-export-data.pdf.

"Choose a Destination (SQL Server Import and Export Wizard)," Mar. 24, 2017, 2 pp., Retrieved From the Internet: https://opbuildstorageprod.blob.core.windows.net/output-pdf-files/en-us/SQL.sql-content/live/integration-services/import-export-data.pdf.

"Create Database (SQL Server Import and Export Wizard)," Mar. 24, 2017, 2 pp., Retrieved From the Internet: https://opbuildstorageprod.blob.core.windows.net/output-pdf-files/en-us/SQL.sql-content/live/integration-services/import-export-data.pdf.

"Specify Table Copy or Query (SQL Server Import and Export Wizard)," Mar. 24, 2017, 3 pp., Retrieved From the Internet: https://opbuildstorageprod.blob.core.windows.net/output-pdf-files/en-us/SQL.sql-content/live/integration-services/import-export-data.pdf.

"Provide a Source Query (SQL Server Import and Export Wizard)," Mar. 24, 2017, 3 pp., Retrieved From the Internet: https://opbuildstorageprod.blob.core.windows.net/output-pdf-files/en-us/SQL.sql-content/live/integration-services/import-export-data.pdf.

"Select Source Tables and Views (SQL Server Import and Export Wizard)," Mar. 24, 2017, 4 pp., Retrieved From the Internet: https://opbuildstorageprod.blob.core.windows.net/output-pdf-files/en-us/SQL.sql-content/live/integration-services/import-export-data.pdf.

"Configure Flat File Destination (SQL Server Import and Export Wizard)," Mar. 24, 2017, 3 pp., Retrieved From the Internet: https://opbuildstorageprod.blob.core.windows.net/output-pdf-files/en-us/SQL.sql-content/live/integration-services/import-export-data.pdf.

"Convert Types Without Conversion Checking (SQL Server Import and Export Wizard)," Mar. 29, 2017, 2 pp., Retrieved From the Internet: https://opbuildstorageprod.blob.core.windows.net/output-pdf-files/en-us/SQL.sql-content/live/integration-services/import-export-data.pdf.

"Column Mappings (SQL Server Import and Export Wizard)," Mar. 24, 2017, 5 pp., Retrieved From the Internet: https://opbuildstorageprod.blob.core.windows.net/output-pdf-files/en-us/SQL.sql-content/live/integration-services/import-export-data.pdf.

"Review Data Type Mapping (SQL Server Import and Export Wizard)," Mar. 24, 2017, 5 pp., Retrieved From the Internet: https://opbuildstorageprod.blob.core.windows.net/output-pdf-files/en-us/SQL.sql-content/live/integration-services/import-export-data.pdf.

"col. Conversion Details Dialog Box (SQL Server Import and Export Wizard)," Mar. 24, 2017, 2 pp., Retrieved From the Internet: https://opbuildstorageprod.blob.core.windows.net/output-pdf-files/en-us/SQL.sql-content/live/integration-services/import-export-data.pdf.

"Create Table SQL Statement (SQL Server Import and Export Wizard)," Mar. 24, 2017, 2 pp., Retrieved From the Internet: https://opbuildstorageprod.blob.core.windows.net/output-pdf-files/en-us/SQL.sql-content/live/integration-services/import-export-data.pdf.

"Preview Data Dialog Box (SQL Server Import and Export Wizard)," Mar. 24, 2017, 1 p., Retrieved From the Internet: https://opbuildstorageprod.blob.core.windows.net/output-pdf-files/en-us/SQL.sql-content/live/integration-services/import-export-data.pdf.

"Save and Run Package (SQL Server Import and Export Wizard)," Mar. 24, 2017, 3 pp., Retrieved From the Internet: https://opbuildstorageprod.blob.core.windows.net/output-pdf-files/en-us/SQL.sql-content/live/integration-services/import-export-data.pdf.

"Save SSIS Package (SQL Server Import and Export Wizard)," Mar. 24, 2017, 4 pp., Retrieved From the Internet: https://opbuildstorageprod.blob.core.windows.net/output-pdf-files/en-us/SQL.sql-content/live/integration-services/import-export-data.pdf.

"Complete the Wizard (SQL Server Import and Export Wizard)," Mar. 24, 2017, 2 pp., Retrieved From the Internet: https://

(56) References Cited

OTHER PUBLICATIONS opbuildstorageprod.blob.core.windows.net/output-pdf-files/en-us/ SQL.sql-content/live/integration-services/import-export-data.pdf.
"Performing Operation (SQL Server Import and Export Wizard)," Mar. 24, 2017, 2 pp., Retrieved From the Internet: https:// opbuildstorageprod.blob.core.windows.net/output-pdf-files/en-us/ SQL.sql-content/live/integration-services/import-export-data.pdf.
"Data Type Mapping in the SQL Server Import and Export Wizard," Mar. 30, 2017, 2 pp., Retrieved From the Internet: https:// opbuildstorageprod.blob.core.windows.net/output-pdf-files/en-us/ SQL.sql-content/live/integration-services/import-export-data.pdf.
"Import Data From Excel to SQL Server or Azure SQL Database," Apr. 14, 2017, 5 pp., Retrieved From the Internet: https:// opbuildstorageprod.blob.core.windows.net/output-pdf-files/en-us/ SQL.sql-content/live/integration-services/import-export-data.pdf.

* cited by examiner

HEALTHCARE CLAIM DATA RECREATION FOR SUPPORT AND ANALYSIS

CROSS REFERENCE TO RELATED APPLICATIONS

The present application claims benefit of U.S. Provisional Patent Application No. 62/271,722 entitled "Healthcare Claim Data Recreation For Support and Analysis," filed Dec. 28, 2015.

TECHNICAL FIELD

The present embodiments are generally directed to systems and processes for obtaining information, and the relationships between that information, from a database, particularly with regards to a healthcare claim.

BACKGROUND

One third of support issues within software products across companies require the issues reproduction in non-production environment. Software analysts and support teams spend a majority of their time, approximately 60%, recreating data specific to client reported issues) so those issues can be researched, fixed, and tested. The time spent on recreation of such issues spikes significantly when the analyst does not have access to the client's data. As a result, analysts rely on other means to recreate the problem and obtain client data, including relying on web meetings or database backups in these situations.

These current methods of getting data from clients are inefficient and typically ineffective.

One such method, web meetings, do not give the flexibility of time as such meetings are driven with the help of the client. These meetings often last too long or take place at unacceptable times, particularly when dealing with support and clients in different time zones. Nor is it acceptable to expect an analyst to look at all possible data and configuration in one or two of these meetings. Even if the analyst has looked at all data, it is a dead end if they are unable to replicate the issue internally for further analysis or fix.

A further issue with current methods is that the data related to the support issue represents whole sets of entities and/or a combination of the underlying entity attributes, all of which are required to recreate a specific scenario-based issue. Thus, this data can reside in 100s or 1000s of different tables depending on the entity schema the given database is modelled. This makes data recreation, in order to recreate and troubleshoot a client's issue, extremely difficult.

Usage of a database backup from the client proves inefficient and ineffective as well. Specifically, such backups cause huge storage issues, especially if a new database (that spans GBs to TBs) has to be shipped for each support issue.

In the rare occasions where the client has provided the analyst with access to the client's database, support could leverage remote debugging to research the issue. However, this creates multiple network challenges. The connection between analyst and client must go through a secure Virtual Private Network (VPN) tunnel (preferably with split tunneling enabled to ensure the analyst's network doesn't go down when accessing the client's network). Network configuration and latency along with data security prevents an overwhelming majority of clients, approximately 85%, from exploring this option. And more and more clients who have traditionally provided this option are turning away from this model in the name of security.

To be effective, the above issues need to be avoided when analyzing a client's issue. That is, there is a real need to make data analysis seamless to clients, consider storage, eliminate security threats, comply with data privacy standards (such as protected health information (PHI) standards), and more importantly provide analysts with all the correct necessary data in a sustainable fashion that can be repeated.

For example, if a client reports a problem with one of their claims, possibly a health care claim, in the system where in it pays $500 while it should only pay $300. In order for the analyst to replicate the same scenario (and related data) in the analyst's internal servers, they would need a similar claim to start with. In order for the analyst to have that claim, they would need the provider who rendered the service and the provider's contract, the patient who got the service along with patient's benefits; the patient's employer information, the policy obtained, and other relevant and/or related information.

Although backing up the entire database and transporting that database to have it restored at the analyst's site is possible, it will require hours of backing up and restoring (depending on the size of the database (db)) and occupy a lot of space that does not make it sustainable or effective. This solution is simply not effective.

Furthermore, using technologies such as Microsoft SQL Servers Import and Export Wizard (https://msdn.microsoft.com/en-us/library/ms140052.aspx) produce inadequate results. These technologies export the entire row in a database that is based on the query and import into a destination of the user's choice. The technology also relies on the user knowing what data is required to extract. These factors, including others, makes it impossible to manually create an extract query when there are hundreds of tables involved.

SUMMARY

One embodiment of the invention is a method for providing software support involving an entity in a database. This method comprises selecting to export information related to an entity to assist in resolving a software support issue. The method further comprises identifying data relevant to said entity. The method further comprises identifying relationships relevant to said entity. The method further comprises creating a data structure containing said entity, data, and relationships. And the method further comprises storing said data structure to enhance the resolution of the software support issue.

Another embodiment of the invention is a computer program for providing software support involving an entity in a database. The computer program comprises computer code for selecting to export an entity to assist in resolving a software support issue. The computer program further comprises computer code for identifying data relevant to said entity. The computer program further comprises computer code for identifying relationships relevant to said entity. The computer program further comprises computer code creating a data structure containing said entity, data, and relationships. And the computer program further comprises computer code storing said data structure to enhance the resolution of the software support issue.

Another embodiment of the invention is a method for providing software support involving an entity in a database. The method comprises selecting to import an entity to assist in resolving a software support issue. The method further comprises importing a data structure identifying said entity and relevant data and relationships to enhance the resolution of the software support issue. The method further comprises storing the entity. And the method further comprises storing the relevant data to said entity; and storing the relevant relationships to said entity.

BRIEF DESCRIPTION OF THE DRAWINGS

The accompanying drawings constitute a part of this specification and together with the specification, illustrate certain exemplary implementations of this disclosure.

DETAILED DESCRIPTION

Figure 1:
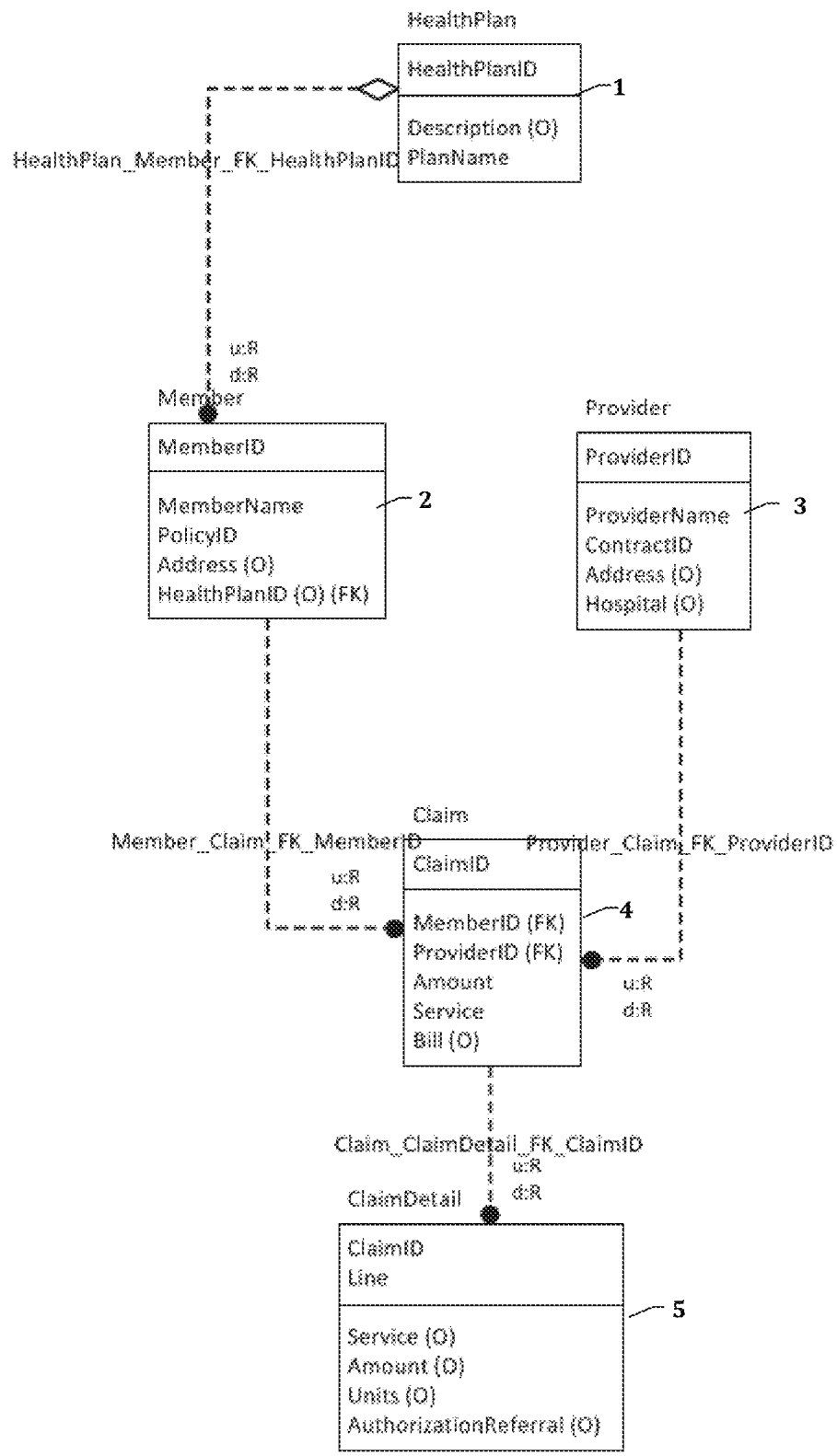
FIG. 1 depicts primary tables related to a claim, including both parent and child tables.

Reference will now be made in detail to the preferred implementations, examples of which are illustrated in the accompanying drawings.

One possible assumption is that, throughout this exemplary embodiment, a Relational Database Management System (RDBMS) is used and the tables are linked using relations correctly or a SQL Server is used and the tables are linked using relations correctly.

Transporting, either over a network or locally, and storing a huge database on a storage device for a single claim is both ineffective and inefficient. Instead, the better approach is to obtain the single claim at issue from the client's database and transfer it to the analyst's database. This will eliminate all the other claims and other data that the analyst does not need to analyze and allow the analyst to correct the client's specific issue.

The benefits of such a process and enhancements it provides are many. The described process reduces the amount of time spent troubleshooting incidents and solving software support issues, potentially regarding specific healthcare claims and/or software, for both the analyst and clients. The analyst will have the data immediately, on day one, for research without the struggle of access or multiple web meetings. The analyst does not need to recreate the data needed, thereby saving time (roughly 60%). There are also no assumptions regarding data, ensuring that research, fixes, and testing are done on actual client issues and not a "close," and possibly inaccurate, replica. The data can also be stored and used for future research or regression testing by the analyst. The described process is also easier to implement in an offshore support model or when using new analysts in support because they can research the code by debugging this data.

The benefits of this process are directed toward software support and debugging, particularly when such support involves data stored in a client's database. The benefits of this process are also directed towards evaluating, improving, and supporting the healthcare claim adjudication and process. The process provides a unique, efficient, and extremely beneficial solution to supporting issues involving client entities, such as claims, that are part of, and link to, other database elements.

The process described in more detail below realizes these benefits by selecting not only the specific claim being analyzed, but also obtaining all of the other required, related data to the claim such as the provider, patient, contract, benefit, policy, and other relevant information. The described process determines all the related tables and data by itself and exports them.

In general, the process can begin at the client, running on a processor on the client's computer. The process can be run on a processor located elsewhere, such as another server or as Software as a Service (SaaS). The process can begin when the client clicks on a link or other user interface object shown on the client's computer. This selection by the client may occur when the client has a problem with a specific entity. This entity can be a claim, member, provider, or other aspect of a healthcare claim or some other type of claim.

The process, continuing to run on a processor at the client's computer or elsewhere, potentially as SaaS, executes an algorithm on a processor to collect all data and relationships stored in any type of memory on any computer and/or server at the client or elsewhere. The process, which includes a series of functions and sequence of function calls, collects data and relationships relevant to the entity the client selected. The described process will collect this entity and its related parent and child records. This data and relationships may include aspect of a member, provider, or other aspect of a healthcare claim at the client. This data and relationships may be stored, and collected, on a local computer at the client or from another server and/or storage device located elsewhere.

The process may use foreign keys and/or primary keys to facilitate the collection of all relevant data and relationships to the entity that are the subject of the client's request. For example, such keys may be used when the described process is running on the client's processor or elsewhere, potentially as SaaS, to obtain information relevant to a particularly healthcare claim.

The process then creates a data structure, such as Extensible Markup Language (XML). This data structure may contain some or all of the data and relationships collected that are relevant or related to the selected entity, which may be a specific claim. The data structure may be stored temporally or permanently in a storage device at the client or remotely.

The data structure can be attached, possibly in XML, to the incident regarding the entity, such as a healthcare claim, that the client submits to the analyst for further research. This may be submitted over a local or wide area network by a variety of means and can be sent from the client's computer, or a related computer, to a server at the analyst.

Parent Tables

All of the information, including data relevant to the process and involved claim(s), is stored in each table in a SQL Server. This information may be stored on a hard drive or other storage device. The SQL Server may be running on a processor local to the client or at another location.

For example, a claim is stored in a claim table while patient information is stored in member table, etc. Since a claim needs a patient, the claim table makes sure that a member record already exists in the member table using a foreign key (FK) relationship. This helps maintain data integrity and allows the use of these FK's to identify the relational data.

Looking at a claim table, such as that shown in FIG. 1, the claim table 4 has a FK for the MemberID and the ProviderID column. This denotes that the MemberID column in the claim is related to the MemberID column in the Member table. The relationship is clearly defined by the FK "Member_Claim_FL_MemberID". This is the same case with the ProviderID. The member table contains a FK which indicates the need for a health plan (via HealthPlanID) to successfully have a member. These are "Parent" tables because without a record in these parent tables, the current (child) table cannot have data in them.

A table can have multiple parent tables and multiple child tables. Using the FK's, one can traverse to the parent and child tables to get related data.

For example, if one needs a specific claim out of the million claims from the claim table, such as that seen in FIG. 1, one would look at the FK's within the claim table. This will indicate the need to get the related Member 2 and Provider 3 for that specific claim (claim 4). Once the related MemberID and ProviderID (contained within 2 and 3, respectively) are obtained for that specific claim 4, one goes to the parent tables that are Member 2 and Provider 3 and get just that specific Provider 3 and Member 2 that was identified from the claim table.

Now since there are no parents for Provider 3, there is no need to go any further. But Member has a parent, which is HealthPlan 1. The same logic is used, which is to identify the one specific HealthPlanID (contained within 1) from that one specific Member 2 that is of interest. And this process continues until all parent tables (in this case until HealthPlan 1) are obtained.

Child Tables

Similar to extracting parent tables, there is also need to extract and import the related data from child tables too. These child tables may be stored in similar manners and at similar, or different locations, as the parent tables.

For example, as seen in FIG. 1, ClaimDetail 5 is a child table to the claim table (claim 4). To extract the claim table, one looks for child tables in a similar manner as parent tables are examined. In this case, a FK points to a child table indicating that CLAIMID has been used in the FK—Claim_Claimdetail_FK_ClaimID. This will again help identify child tables so that one can go and extract the specific claim record from the child tables as well.

Algorithm and Related Export Process

The export process, including the algorithm, is run on a processor and accesses the storage device(s) that contain the relevant parent and child tables, and other data and relationships, described above. The export process, including the algorithm, may run on multiple processors, possibly running solely at a computer local to the client, possibly running partially at the client and then partially at another processor located elsewhere, or possibly running entirely remotely, potentially as SaaS.

The export process, typically a computer program, is invoked with basic set of parameters consisting of the primary table, field name, and a value which comes from the client's product when the client reports an issue.

The export process, including the algorithm, can be started by the client, on a processor, by simply selecting a claim, or claims or other entities, and clicking an export button. This selection can occur on the same processor that will run the process (and algorithm) or started on another, remote processor. The selection can be done via any user or graphical interface running on a processor. The selection will start the process on the relevant processor and, eventually, send the relevant data, over a network if required, to the analyst's server and/or processor or to other relevant support computers.

Figure 2A:
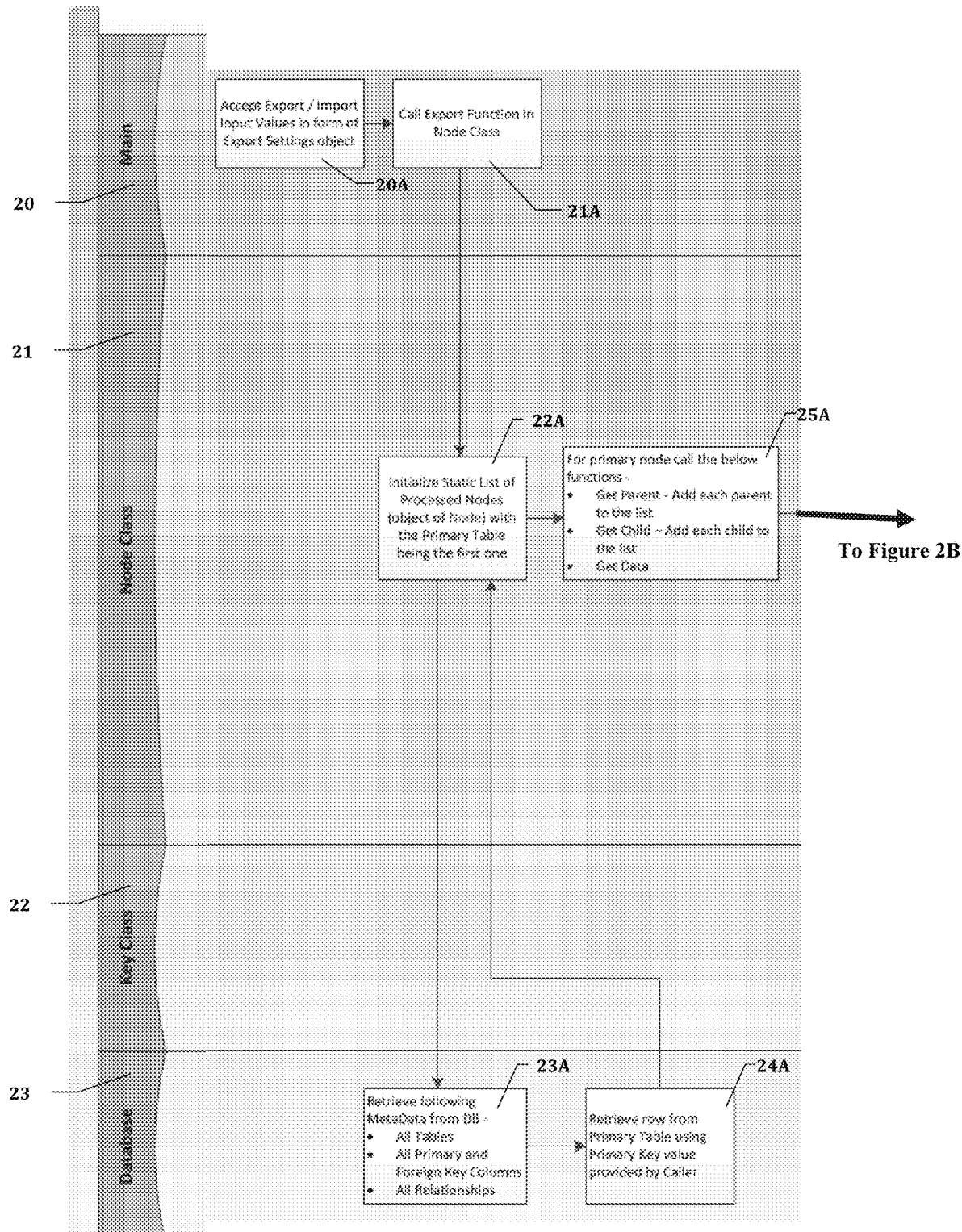
FIGS. 2A-2C show in detail the specific steps of the export process.
Figure 2B:
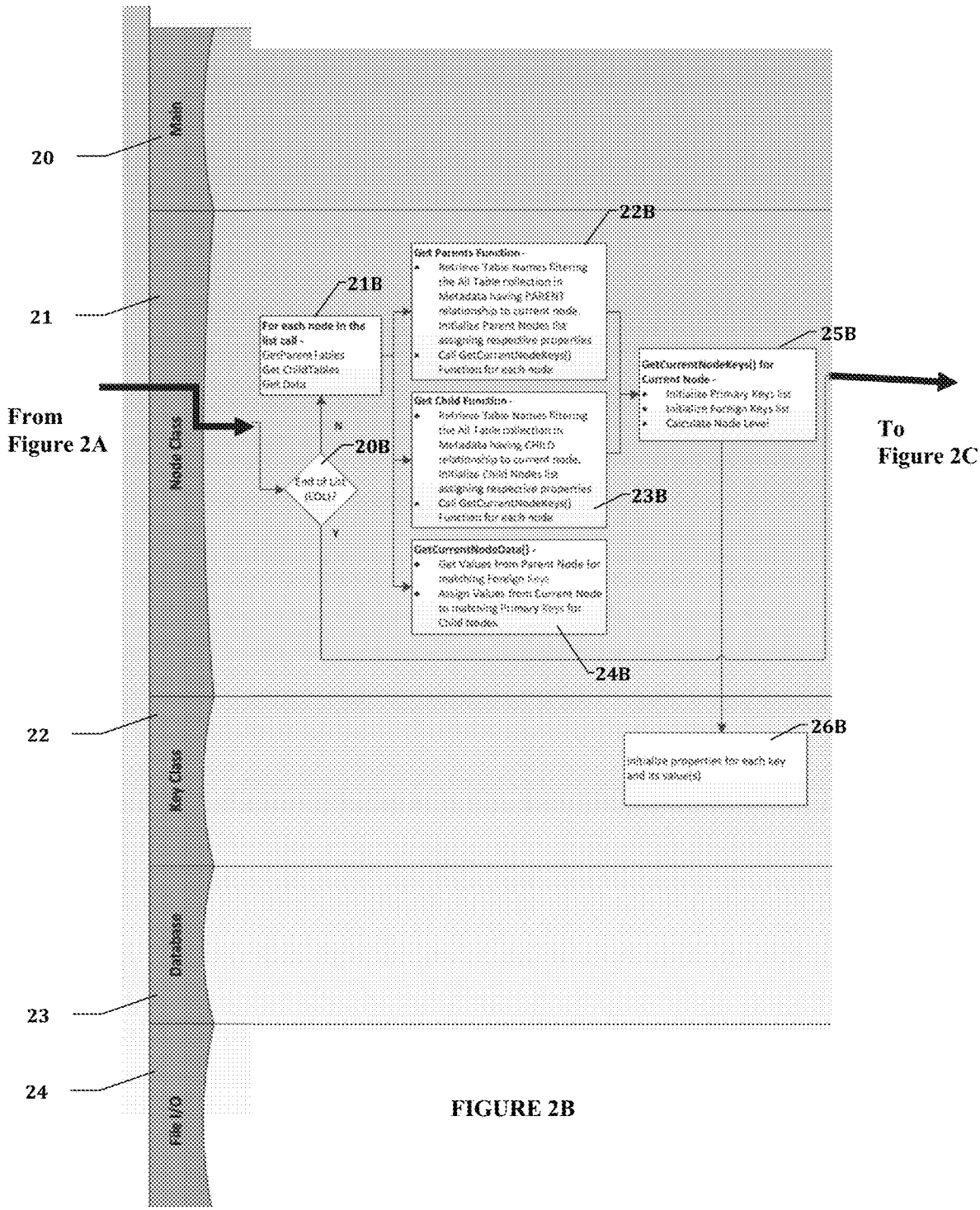
Figure 2C:
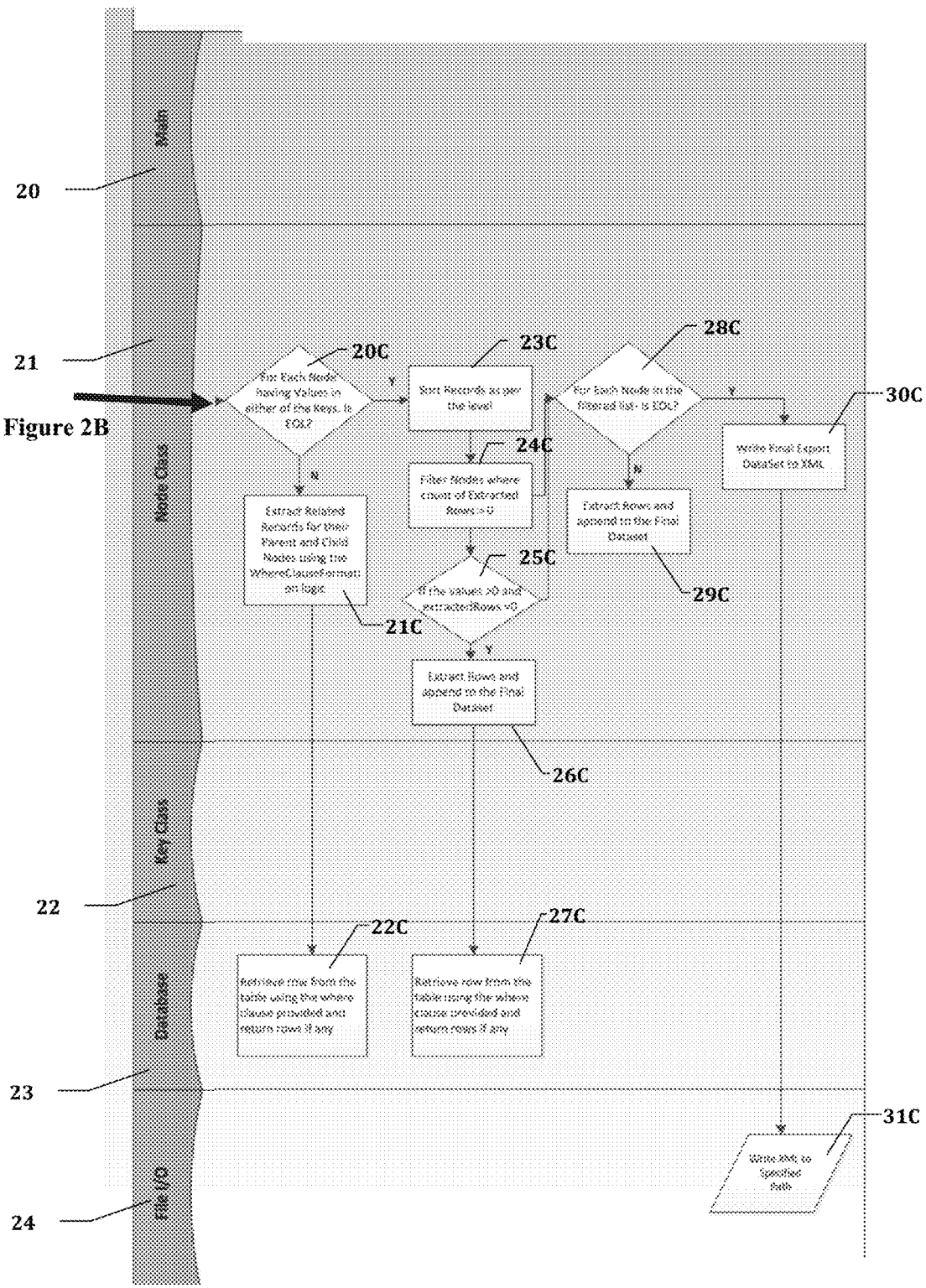

The step by step flow (or sequence) of the process is detailed below. The process runs on a processor, or processors. An example of the process visually depicted in FIGS. 2A-2C. FIGS. 2A-2C include swimlanes to the left to provide context where each block is executed, including. FIG. 2A includes swimlanes for Main 20, Node Class 21, Key Class 22, and Database 23. FIG. 2B and FIG. 2C includes the same swimlanes as FIG. 2A (Main 20, Node Class 21, Key Class 22, and Database 23) and add a swimlane for File I/O 24.

The export process begins with the acceptance of export and/or input values, which can be in the form of an Export Setting object. The user provided values for the initial table and primary key are then used to retrieve the main record and store it in the object. This is shown in 20A in FIG. 2A.

Figure 3:
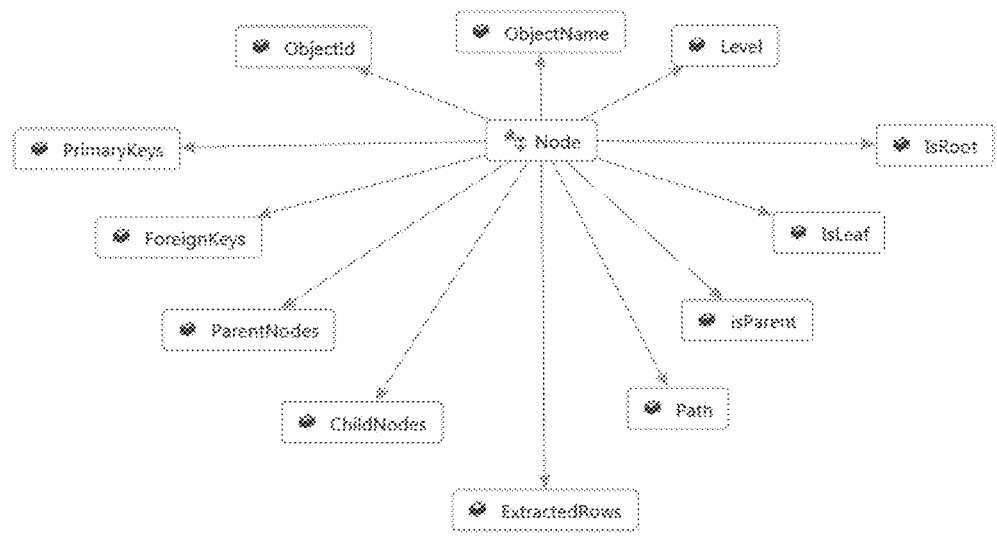
FIG. 3 details the node and exemplar fields and methods associated with the node class.

Next, an export function is begun for a particular node class. This can be a call to Export Function in node class, shown as 21A in FIG. 2A. An exemplar list of fields and methods for the node class are depicted in FIG. 3.

The process then initializes the collection of nodes. An example of this step is 22A in FIG. 2A. The collection of nodes is also sometimes referred to as processedNodes. The collection of nodes is with a primary node based on the values provided by client. The collection may also be with the primary table being the first one.

Every node is a self-contained entity which is responsible for its own data and behavior. At any instance, a node will know it's parent nodes, child nodes, primary keys, and foreign keys, and data collected during the export process. The structure of a node object is highly influenced by a hierarchical (tree-like) data in relational database, and shown in FIG. 3. Thus, this enables the process to be run on any relational database management systems available in the market.

Figure 4:
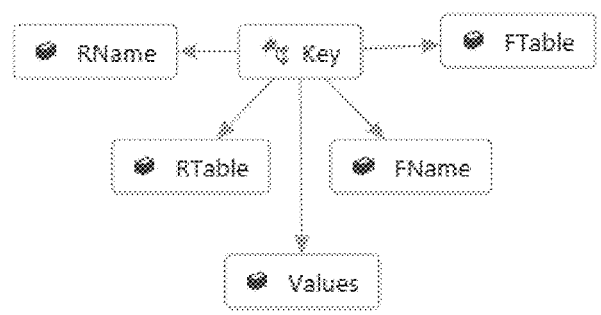
FIG. 4 provides an example of a key and its related fields.

The key entity defines the tables and column it links. An example of a key, including its fields is detailed in FIG. 4.

Figure 5:
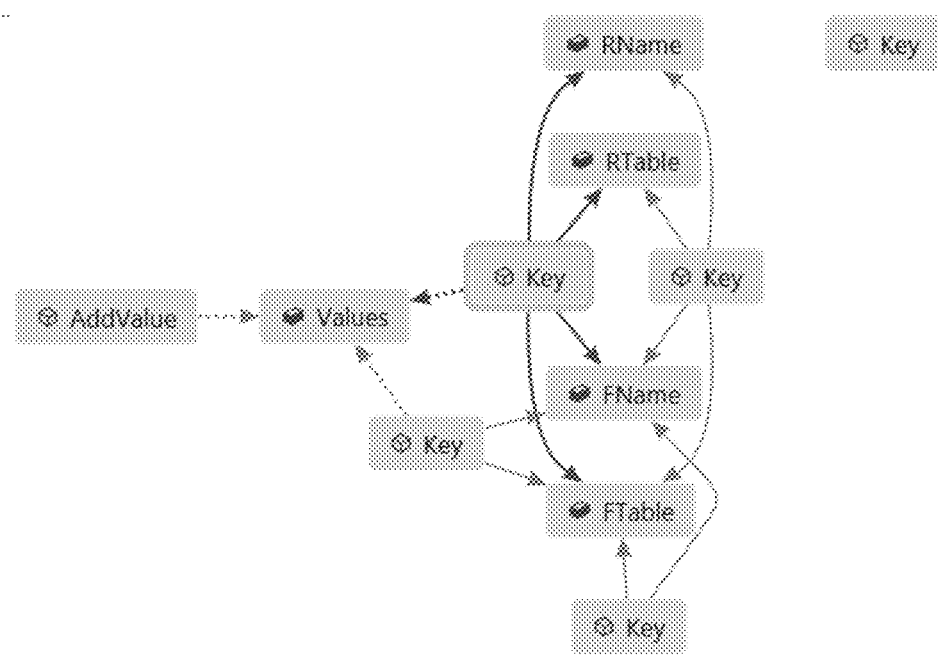
FIG. 5 graphically depicts the relationship between keys and tables and values

A static object is then created at the start of extraction process that reads from the database schema of the primary transactional database—all tables, primary key and foreign key columns and relationships. This serves as a primary reference for traversal for every given node the primary node is linked to. FIG. 5 graphically depicts part of this process, and how keys relate to tables and values.

Examples of these steps are shown in FIG. 2A, where the metadata from the database (DB) is retrieved 23A, including all tables, all primary and foreign key columns, and all relationships. Then, in 24A, a row is retrieved from the primary table using the primary key value provided. Part of the process of reading from the database is also depicted relationally in FIG. 5.

The process then invokes the following algorithm that uses various input, builds the entire database schema, initiates it with the primary table as the first node, traverses through all the relationally linked tables, and collects values for each node while traversing them.

The algorithm is recursive, collecting the parents, children, keys and data for each node starting with the primary node (e.g., 25A in FIG. 2A and [22B-24B] in FIG. 2B). This may be done using a "for" loop, collecting parent, child and key metadata for each node using the various functions described below.

An example of this loop is shown in FIG. 2B, first checking whether the list has ended 20B, and if not, calling functions to get parent, child and data information for each node [ ]. These specific functions are depicted in 22B (parent function), 23B (child function), and 24B (data function). And once these functions are called, the node keys for the current node are retrieved 25B, with the properties for each key and its value(s) being initialized if necessary 26B.

The algorithm maintains a static list of all tables traversed with initial node being inserted at first. The tree structure is stored in the form of list, the list potentially being named processedNodes, which consists of every node that needs to be included.

Then, the final steps in the export logic are to filter the list of node that have extracted rows populated (20C-29C in FIG. 2C) and sort them based on the level.

This sorted and filtered list is then extracted as XML file using XMLDataHelper class (detailed in 94 in FIG. 9), or something similar, (30C in FIG. 2C) and ready to be transported via secure means. The final dataset can then be written to XML, possibly using XMLDataHelper class, to the file path provided by user (31C in FIG. 2C).

In addition, the process may generate logs from each function and step mentioned above and collect in a single log file along with the exported data XML. Alternatively, the list of records traversed will be collected in a log file placed under the same directory as XML.

The above process, and included algorithm, will work with most databases, particularly those that are fully integrated and/or having the necessary and proper links and keys.

Process can be started with any information regarding the claim. From this starting point, the process, and including algorithm, is able to obtain all relevant information to the claim.

Primary Functions Detailed

There are a variety of primary functions used in this algorithm part of the process. While not exhaustive, the primary functions are described in more detail below.

These functions may use one or more of these common objects:

TableRelationshipMaster—Holds all tables, columns linked as parent and child tables based on foreign key relationships TablePrimaryKeysMaster—Holds all the tables and columns defined as primary keys TableForeignKeyMaster—Holds all the foreign keys columns and tables linked with the columns DatabaseEngine—Database helper class to retrieve data from a database ProcessedNodes—List of all the node objects traversed and to be extracted for a given input Check IfRoot( ) function—Identify if the current node is one of the root nodes. This helps in determining if the GetParents( ) function needs to be called or not and determining the level of the object, considering level is defined as 0 for root and n−1 for the nth child in the hierarchy (leaf node).

Check IfLeaf( ) function—Identify if the current node is one of the leaf nodes. This helps in determining if the GetChild( ) function needs to be called or not and determining the level of the object, considering level is defined as 0 for root and n−1 for the nth child in the hierarchy (leaf node).

GetParents( ) function (also identified as Get Parents function 22B in FIG. 2B)—within the Get Parents function or method the following is typically performed—
  i. Retrieve value from metadata filtered by the current node name.
  ii. Check if the retrieved parent table is a root table (possibly using Check IfRoot( ) function), so that no further GetParents( ) can be called on that node
  iii. Calculate its level—Initial node by default may have 0 as starting level. Node may be assigned −1 when it is first added to the list and will be updated upon traversing the related nodes. Any node traversed using GetParents( ) will be assigned currentnode.level+1
  iv. Maintain the traversing path and relationship—this will help in controlling the depth of traversing algorithm
  v. (Optionally) Retrieve the primary and foreign keys and their values using GetCurrentNodeKeys( ) (also referred to as Get Keys)

An example of pseudo-code for the GetParents( ) function follows:

```
GetCurrentNodeParentTables
If CurrentNode.IsRoot is false then
    If CurrentNode.ParentNodes.Count = 0
        Set filter condition where Parent_Table <>CurrentNode.
        Name and Child_Table = CurrentNode.Name
        Apply filter to TableRelationshipsMaster to get
        Parent_Tables for CurrentNode, store these in ParentTables
        Add each ParentTable from ParentTables to
        CurrentNode.ParentNodes with properties
            ObjectId = ParentTable.ID
            ObjectName = ParentTable.Name
            Level = CurrentNode.Level + 1
            IsRoot = CheckRoot(ParentTable)
            Path = ParentTable.Name + CurrentNode.Path
            IsParent = true
        For each CurrentNode.ParentNode
            Call GetCurrentNodeKeys( );
        End For
    End If
End if
```

GetChild( ) function (also identified as Get Child Function 23B in FIG. 2B)—within the Get Child function or method the following is typically performed—
  i. Retrieve value from metadata filtered by the current node name.
  ii. Check if the retrieved child table is a leaf table (possibly using Check IfLeaf( ) function), so that no further GetChild( ) method can be called on that node
  iii. Calculate its level—Initial node by default may have 0 as starting level. Node by default may have n−1 as starting level. Any node traversed using GetParents( ) or GetChild( ) will be assigned currentnode.level−1
  iv. Maintain the traversing path and relationship—this will help in controlling the depth of traversing algorithm
  v. (Optionally) Retrieve the primary and foreign keys using GetCurrentNodeKeys( ) (also referred to as Get Keys)

An example of pseudo-code for the GetChild( ) function follows:

```
GetCurrentNodeChildTables
    If CurrentNode.IsLeaf is false then
        If CurrentNode.ChildNodes.Count = 0
            Set filter condition where Parent_Table = CurrentNode.
            Name and Child_Table <>CurrentNode.Name
            Apply filter to TableRelationshipsMaster to get
            Child_Tables for CurrentNode, store these in ChildTables
            Add each ChildTable from ChildTables to
            CurrentNode.ChildNodes with properties
                ObjectId = ChildTable.ID
                ObjectName = ChildTable.Name
                Level =CurrentNode.Level − 1
                Path = CurrentNode.Path + ChildTable.Name
                IsLeaf = CheckLeaf(ChildTable)
            For each CurrentNode.ChildNode
                Call GetCurrentNodeKeys( );
            End For
        End If
    End if
```

CurrentNodeKeys( ) Function (referenced in 25B in FIG. 2B and also referred to as Gets keys for the current node)—this function performs different actions based on the current state of the node i. If the current node doesn't have primary and foreign keys populated, it retrieves the key data from metadata tables.

ii. Once the key data is available, it looks for related column in its parent and child nodes. If related column is found and has data populated, it adds the value to the respective key in the current node.

iii. If any of the primary keys have a value and if the respective records are not present in the extracted rows list of current node, the function will retrieve data from the database (DB) for the specific primary key and add it to extracted rows.

iv. If there are any records present in extracted rows, the function will search for any foreign keys that match the columns and assign value to the respective foreign keys.

An example of pseudo-code for the GetCurrentNode-Keys( ) function follows:

```
GetCurrentNodeKeys
Try
    // Get values and data for all primary keys of CurrentNode
    If CurrentNode.PrimaryKeys.Count = 0
        Set filter condition where Parent_Table = CurrentNode.Name
        Apply filter to TablePrimaryKeysMaster to get Primary_Keys
        for CurrentNode, store these in PrimaryKeys
        Add each PrimaryKey from PrimaryKeys to CurrentNode.
        PrimaryKeys with properties
            Set FTable = PrimaryKey.TableName
            Set FName = PrimaryKey.ColumnName
            For each valueRow in CurrentNode.ExtractedRows
                If valueRow.ColumnName.Value is not empty
                    Add valueRow.ColumnName.Value to
                    CurrentNode.Values
                End If
            End For
    Else If CurrentNode.ExtractedRows.Count > 0
        For each PrimaryKey in CurrentNode.PrimaryKeys
            If CurrentNode.ExtractedRows.PrimaryKey.ColumnName.
            Value is not empty
                Add
                CurrentNode.ExtractedRows.PrimaryKey.ColumnName.
                Value to PrimaryKey.Values
            End If
        End For
    Else
        For each PrimaryKey in CurrentNode.PrimaryKeys
            If WhereClause is Empty
                Set WhereClause = "select * from" + PrimaryKey.Ftable + " where"
            End if
            For each value in PrimaryKey
                Set WhereClause += value + ","
            End For
            Set WhereClause = WhereClause.Remove(WhereClause.
            LastIndexOf(",", 1)
            Set WhereClause += ' AND '
        End For
        Set WhereClause = WhereClause.Remove(WhereClause.
        LastIndexOf(" AND ", 5)
        listExtractedRows = DatabaseEngine.RetrieveRow(WhereClause)
        If listExtractedRows. Count > 0
            For each row in listExtractedRows
                If row does not exist in CurrentNode.ExtractedRows
                    Add row to CurrentNode.ExtractedRows
                End If
            End For
        End If
    End If
    // Get values and data for all foreign keys of CurrentNode
    If CurrentNode.ForeignKeys.Count = 0
        Set filter condition where FK_Table = CurrentNode.Name
        Apply filter to TableForeignKeysMaster to get Foreign_Keys
        for CurrentNode, store these in ForeignKeys
        Add each ForeignKey from ForeignKeys to CurrentNode.
        ForeignKeys with properties
            Set FTable = ForeignKey.FKTableName
            Set FName = ForeignKey.FKColumnName
            Set RTable = ForeignKey.PKTableName
            Set RName = ForeignKey.PKColumnName
            For each valueRow in CurrentNode.ExtractedRows
                If valueRow.FKColumnName.Value is not empty
                    Add valueRow.FKColumnName.Value to
                    CurrentNode.Values
                End If
            End For
        Set filter condition where CurrentNode.ForeignKeys.RTable =
        CurrentNode.Name
        Apply filter to CurrentNode.ForeignKeys, store these in
        selfRefKeys For each selfRefKey in selfRefKeys
            If CurrentNode.PrimaryKeys.FTable = CurrentNode.Name
                Set CurrentNode.PrimaryKey.Values = selfRefKey.values
            End If
            listExtractedRows = DatabaseEngine.RetrieveRow
            (CurrentNode.Name, selfRefKey.Fname, skey.Values)
            If listExtractedRows. Count > 0
                For each row in listExtractedRows
                    If row does not exist in CurrentNode.ExtractedRows
                        Add row to CurrentNode.ExtractedRows
                    End If
                End For
            End If
        End For
    Else if (CurrentNode.ExtractedRows.Count>0)
        For each ForeignKey in CurrentNode.ForeignKeys
            If CurrentNode.ExtractedRows.ForeignKey.ColumnName.
            Value != ""
                Add
                CurrentNode.ExtractedRows.ForeignKey.ColumnName.
                Value to ForeignKey.Values
            End If
        End For
    End If
End Try
```

GetCurrentNodeData( ) Function (identified as 24B in FIG. 2B and also referred to as Get Current Node Data for the current node)—adds current node to the global list of processed nodes. The function then traverses through each node in the static list and gets its parent and child objects using the following steps— a. Runs this loop for each parent and child node for current node
   i. Adds the parent/child node to the static list if not present. If already present, merge the primary and foreign keys values from both the instance and update object in the list
   ii. For every parent node of current node, checks if its exported rows contains data. If yes, for each foreign key relationship between current and parent node, add the missing values from parent Node to current node. This will be used to extract data for current node
   iii. Similarly for each every child node of current node, check if its exported rows contains data. If yes, for each primary key relationship between current and child node, add the values from foreign key of child node to current nodes primary key. Also add value from primary key of current node to the foreign and primary keys. This ensures that when data is extracted for child node, it includes data referenced by current node as well.
   iv. (Optional) For parent table
      1. Retrieve its row using the value in foreign key.
      2. Get it keys using GetKeys( ) function (also referred to as GetCurrentNodeKeys( ) function) and assign value from extracted record to respective keys
   v. (Optional) For child tables get it keys using GetKeys( ) function (also referred to as GetCurrentNodeKeys( ) function) and adds the value from available primary keys to its foreign keys. It extracts once all the foreign keys have a specific value or after all the nodes are processed.

An example of pseudo-code for the GetCurrentNodeData( ) function follows:

```
        GetCurrentNodeData
Try
    If ProcessedNodes does not contain CurrentNode
        ProcessedNode.Add(CurrentNode)
    End If
    // Assign Values for Parent Nodes
    For each ParentNode in CurrentNode.ParentNodes
        // Check if ParentNode already exists in ProcessedNodes
        If ParentNode is in ProcessedNodes
            Set objNode
            If ParentNode != objNode
                Merge values from ParentNode to objNode
            End if
        Else
            Add ParentNode to ProcessedNodes
        End if
        // Check if ParentNode.PrimaryKey values are present in respective
        CurrentNode.Foreignkey.Values
        If CurrentNode.ExtractedRows.Count > 0
            For each ForeignKey in CurrentNode.ForeignKeys
                If ForeignKey.Rtable = ParentNode.ObjectName
                    If ForeignKey.RName.values.Count > 0
                        ParentNode.PrimaryKey.FName.Values.Add
                        (ForeignKey.RName.Values)
                    End If
                End If
            End For
            Call ParentNode.GetCurrentNodeKeys( )
        End If
    End For
    // Assign Values for Child Nodes
    For each ChildNode in CurrentNode.ChildNodes
        // Check if ChildNode already exists in ProcessedNodes
        If ChildNode is in ProcessedNodes
            Set objNode
            If ChildNode != objNode
                Merge values from ChildNode to objNode
            End If
        Else
            Add ChildNode to ProcessedNodes
            Call ChildNode.GetCurrentNodeKeys( )
        End if
        //Check if all ForeignKey Values of ChildNode are present
        in respective CurrentNode.PrimaryKey.Values
        If ChildNode.ExtractedRows.Count > 0
            For each ForeignKey in ChildNode.ForeignKeys
                If ForeignKey.Rtable = CurrentNode.ObjectName
                    For each value in ForeignKey.RName.values
                        For each PrimaryKey in CurrentNode.PrimaryKeys
                            If PrimaryKey.FTable = ForeignKey.Rtable
                                If PrimaryKey.FName =
                                ForeignKey.RName
                                    If PrimaryKey.Values does
                                    not contain
                                    ForeignKey.Value
                                        Add
                                        ForeignKey.Value to
                                        PrimaryKey.Values
                                    End If
                                End If
                            End If
                        End For
                    End For
                End If
            End For
        End If
        //Check if all PrimaryKey Values of CurrentNode are present
        in respective ChildNode .PrimaryKeys and ChildNode.Foreign-
        Keys
        For each PrimaryKey in CurrentNode.PrimaryKeys
            For each ForeignKey in ChildNode.ForeignKeys
                If PrimaryKey.FTable = ForeignKey.Rtable
                    If PrimaryKey.FName = ForeignKey.RName
                        If ForeignKey.Values does not contain
                        PrimaryKey.Value
                            Add PrimaryKey.Value to
                            ForeignKey.Values
                        End If
                    End If
                End If
            End For
            For each CPrimaryKey in ChildNode.PrimaryKeys
                If PrimaryKey.FName = CPrimaryKey.RName
                    If PrimaryKey.FName = CPrimaryKey.FName
                        If CPrimaryKey.Values does not contain
                        PrimaryKey.Value
                            Add PrimaryKey.Value to CPrimaryKey.Values
                        End If
                    End If
                End If
            End For
        End For
    End For
End Try
```

ExtractRelatedRecords Function—for every node in processedNodes list where either the foreign keys or primary keys have values (20C in FIG. 2C), this function extracts the related records for current node using WhereClauseFormation logic based on the relationship (primary or foreign key) with the current node (as shown as 21C-22C in FIG. 2C). The function may also do the following:
   i. For multiple values for a single foreign key—the individual values need to be included in the where clause as a list e.g. where columnX in ('value1', 'value2' . . . )
   ii. For multiple foreign keys with same table—the values for each key will have to be included in the where clause with and operator (where columnX='value1' and columnY='value1')

iii. (Optionally) For every primary key relationship append the next primary key with 'AND' as to select the exact row we need it to match every primary key value.

iv. (Optionally) For every foreign key relationship, check whether the current node is a child. If yes, append the next foreign key with 'OR' as to select the row in child table it needs to match any of the values. If no, append the foreign key with 'AND' as to select the row that matches all the values of the given column.

Alternatively, the ExtractRelatedRecords function will sort a list of processed nodes based on the level, and extracted row for each node will be merged into a single dataset. If a row is not present, the function will check if the foreign/primary key values are present and extract the row from database using the below where clause conditions.

An example of pseudo-code for ExtractRelatedRecords( ) function follows:

ExtractRelatedRecords(varNode) Set fNode=processedNodes.Find where ObjectName=varNode.ObjectName Call fNode.GetCurrentNodeData( ) Set fKeys=varNode.Find where varNode.ForeignKeys.Values.Count>0 Set pKeys= varNode.Find where varNode.PrimaryKeys.Values. Count>0

```
If pKeys.Count > 0
    For each pKey in pKeys
        For each value in pKey
            Set whereClause += value
        End For
    End For
End If
If varNode.isParent = false
    If fKeys.Count > 0
        For each fKey in fKeys
            For each value in fKey
                Set whereClause += value
            End For
        End For
    End If
End If
If whereClause is not empty
    Results = Call DatabaseEngine.RetrieveData(whereClause)
    If Results. Count > 0
        For each row in Results
            If fNode.ExtractedRows does not contain row
                fNode.Add(row)
                Call fNode.GetCurrentNodeKeys( )
            End if
        End For
    End If
    fNode.GetCurrentNodeData
End If
```

Import Process

Figure 6:
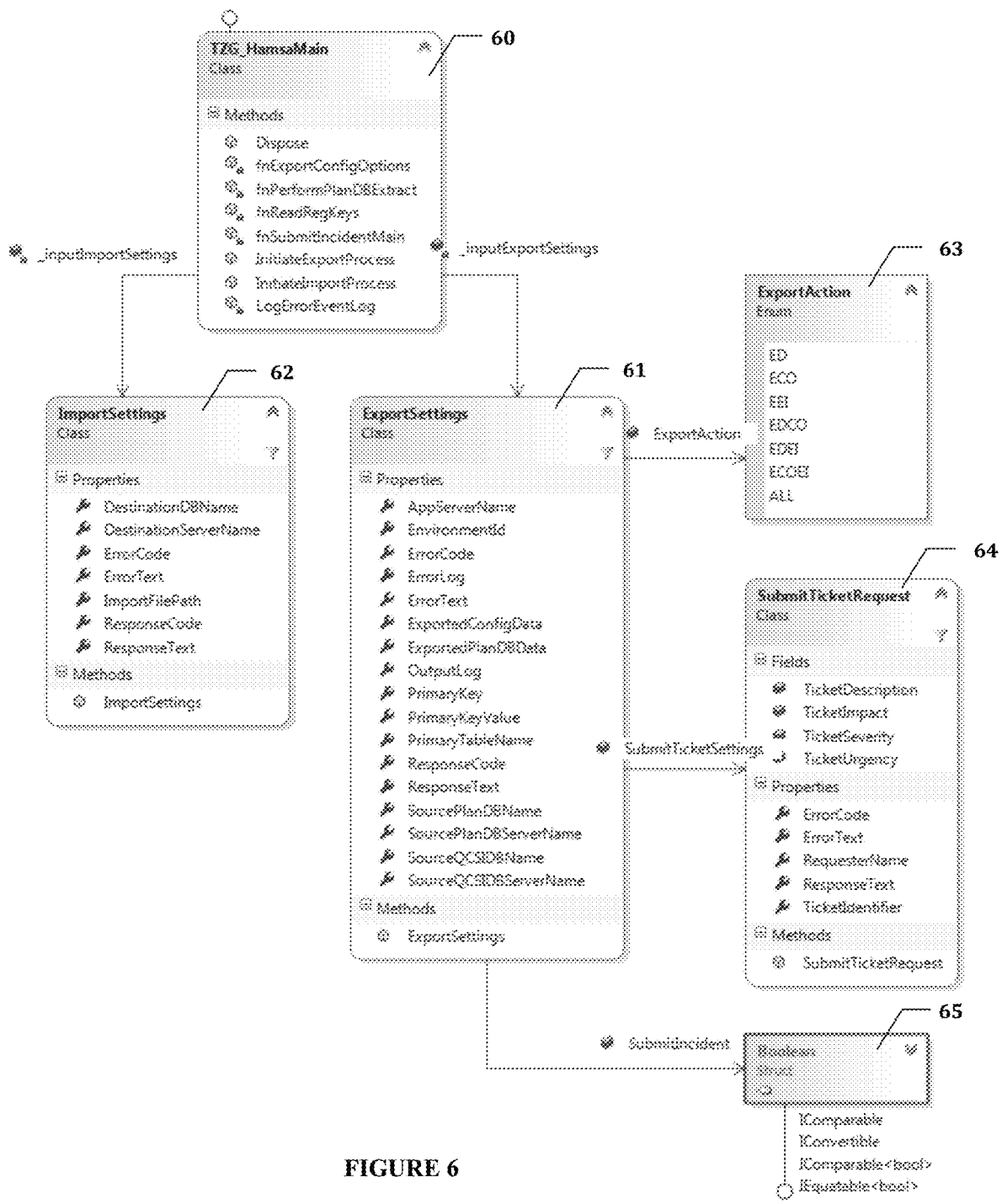
FIG. 6 provides an example of a claim diagram for an individual layer, namely the entity layer, which includes both the ImportSettings and ExportSettings class.

The import process is started in a similar fashion as the client export process described above. The analyst can click a button or other user interface device and the data and relationships are imported. The importation process runs on a processor and creates the relevant portions of the exported client data and relationships. All of the information relevant to the claim and its processing is imported. Importation includes storing, either permanently or temporarily, the relevant portions of the exported client data and relationships on a storage device either located locally, at the analyst, or remotely. An example of the related ImportSettings Class, including a list of its properties, is shown in FIG. 6.

The claim specific and related data can be stored somewhere (like in XML). The data can be imported into any database with a similar schema, any number of times, and stored on a storage device. This would be possible because not only is the claim table exported, but the related parent tables are exported in order for that claim to be created successfully. For example, while importation is occurring, the HealthPlan record, showing in FIG. 1 as 1, is first inserted and then the Member 2 followed by the Provider 3 and then the claim 4, all also shown in FIG. 1.

And during import, child tables can be imported after importing the parent tables. The storage of this information on a storage device is not huge because it has very limited information. It also makes it very easy to send across in an email or by attaching it to a service desk ticket.

Classes for Individual Layers

The process can also be described via class diagrams for individual layers.

One layer relevant to the export and import process is the entity layer. The entity layer includes the main class, 60, in FIG. 6 and contains various methods, including InitiateExportProcess. The beginning of the export process to submit an incident to an analyst initially uses the properties and methods defined in the ExportSettings class 61. From here, an ExportAction 63 occurs, along with SubmitTicketRequest class 64, including specific fields and properties, and a SubmitIncident Boolean structure 65.

From the main class, a client may also InitiateImportProcess from the main class 60. This invokes specific properties and methods defined by the ImportSettings class 62.

Figure 7:
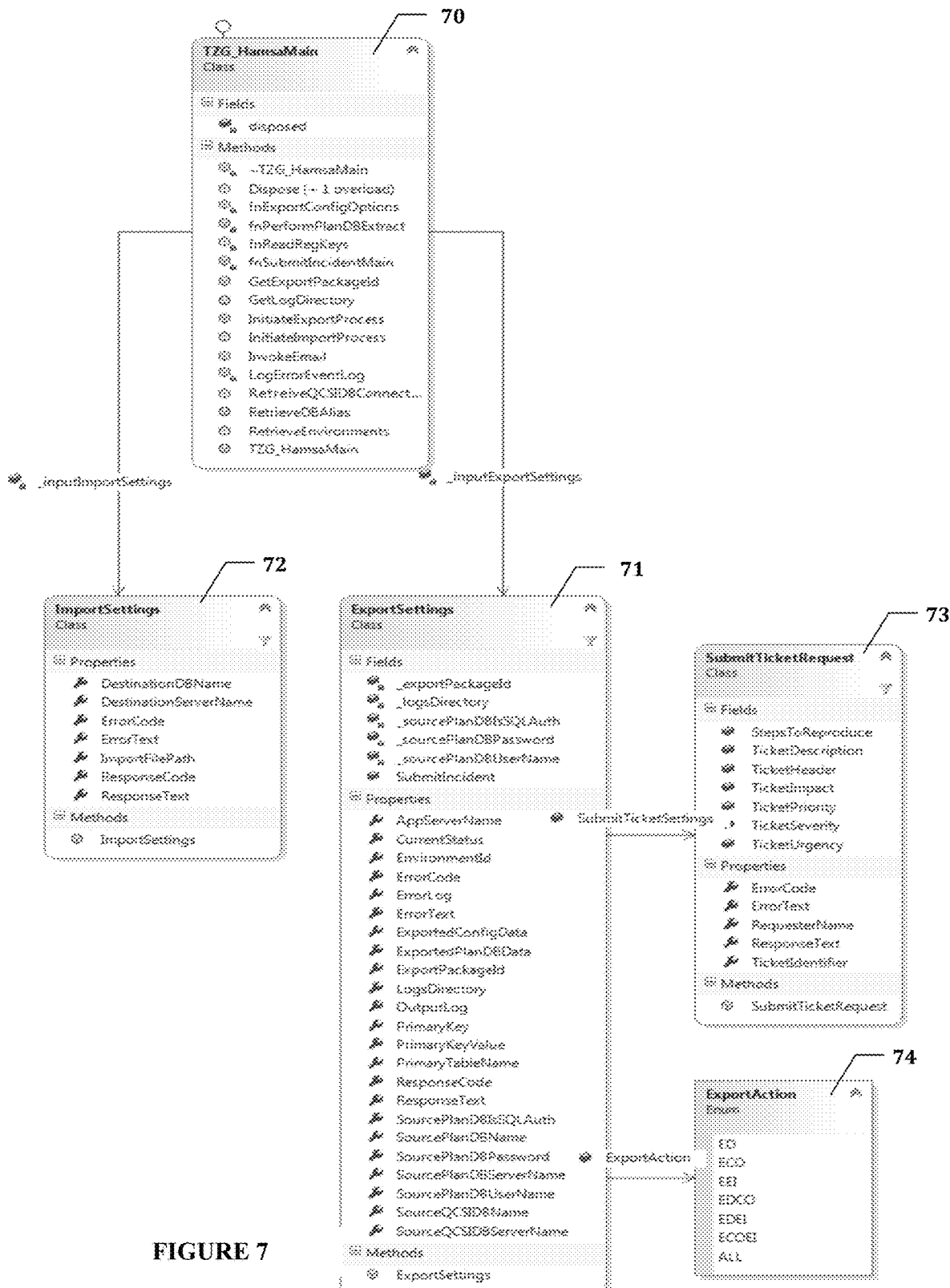
FIG. 7 provides another example of a claim diagram for an individual layer, namely the entity layer, which includes both the ImportSettings and ExportSettings class.

An alternative class depiction of this portion of the entity layer is shown in FIG. 7. This alternative includes a main class, 70, an ExportSetting 71 and ImportSetting 72. This alternative also includes a SubmitTicketRequest class 73 and an ExportAction 74.

Figure 8:
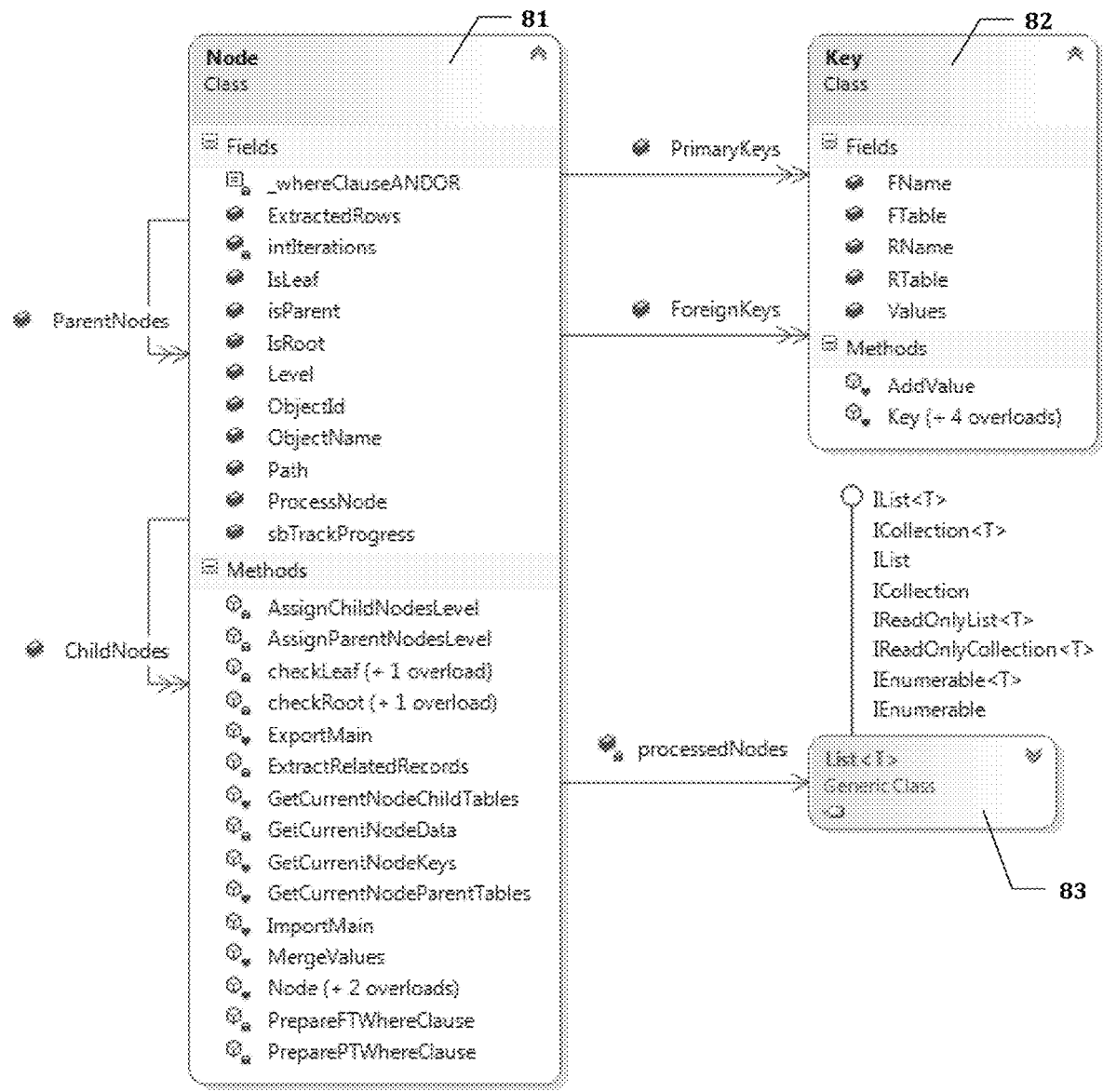
FIG. 8 depicts a claim diagram for an individual layer, namely the entity layer, which includes the Node class.

The entity layer also includes the Node class, 81 in FIG. 8, which contains the listed fields and methods. A Node knows its ParentNodes and ChildNodes as well as its PrimaryKeys and ForeignKeys, the latter two part of the Key class 82 including the defined fields and methods. The collection of nodes via the process described herein is shown as processedNodes 83. FIG. 8 shows the classes involved in the process shown in FIG. 2B and described above.

Figure 9:
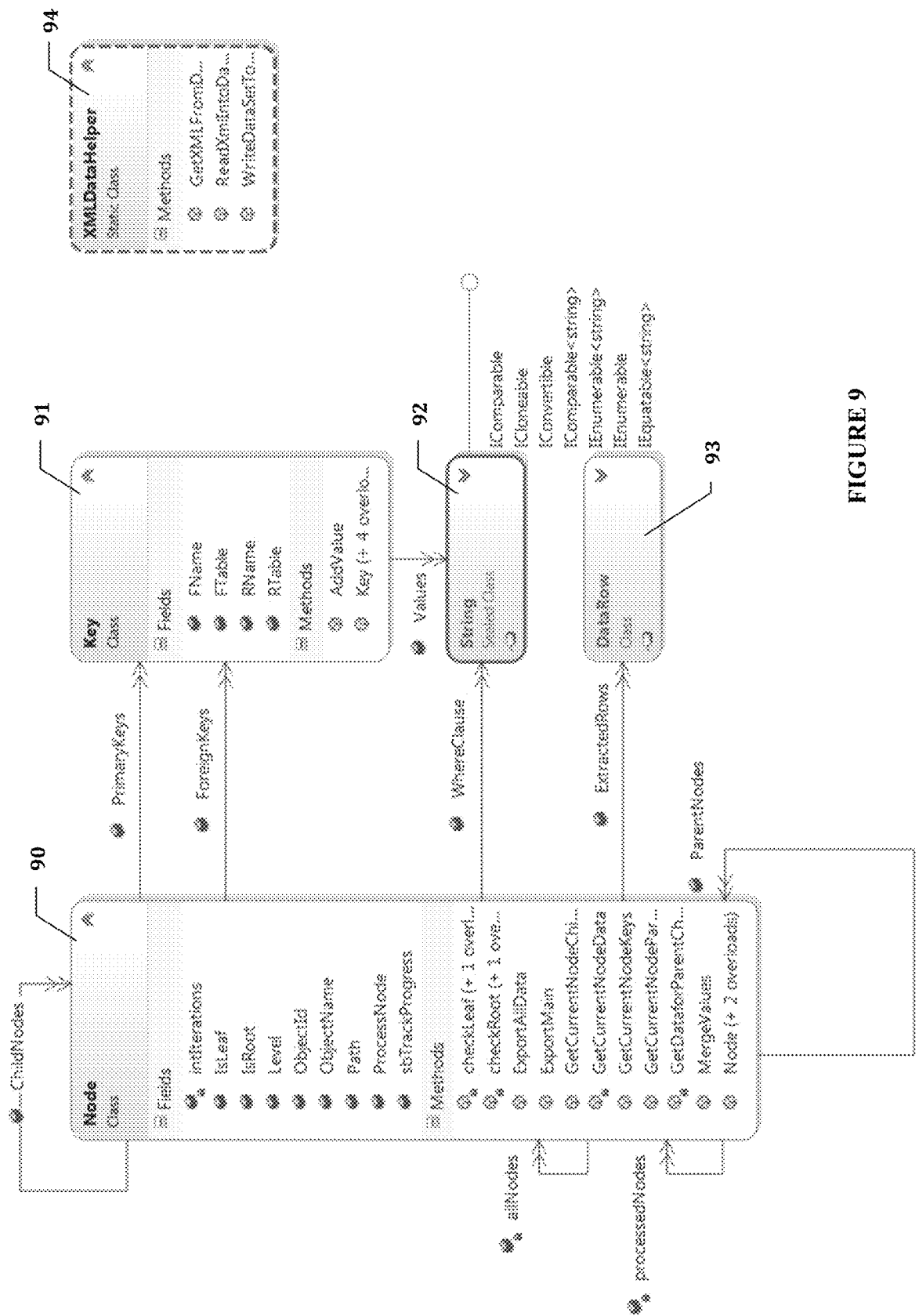
FIG. 9 provides another example of a claim diagram for an individual layer, namely the entity layer, which includes the Node class.

FIG. 9 provides an entity layer, class depiction of some of the process shown in FIG. 2C. The Node class 90 and Key class 91 are again depicted. FIG. 9 also includes the WhereClause 92 and ExtractedRows 93. The XMLDataHelper class 94 used to extract the sorted and filtered list produced using the process in FIG. 2C is also shown. The XMLDataHelper may also be used to extract data to a specific file path.

Figure 10:
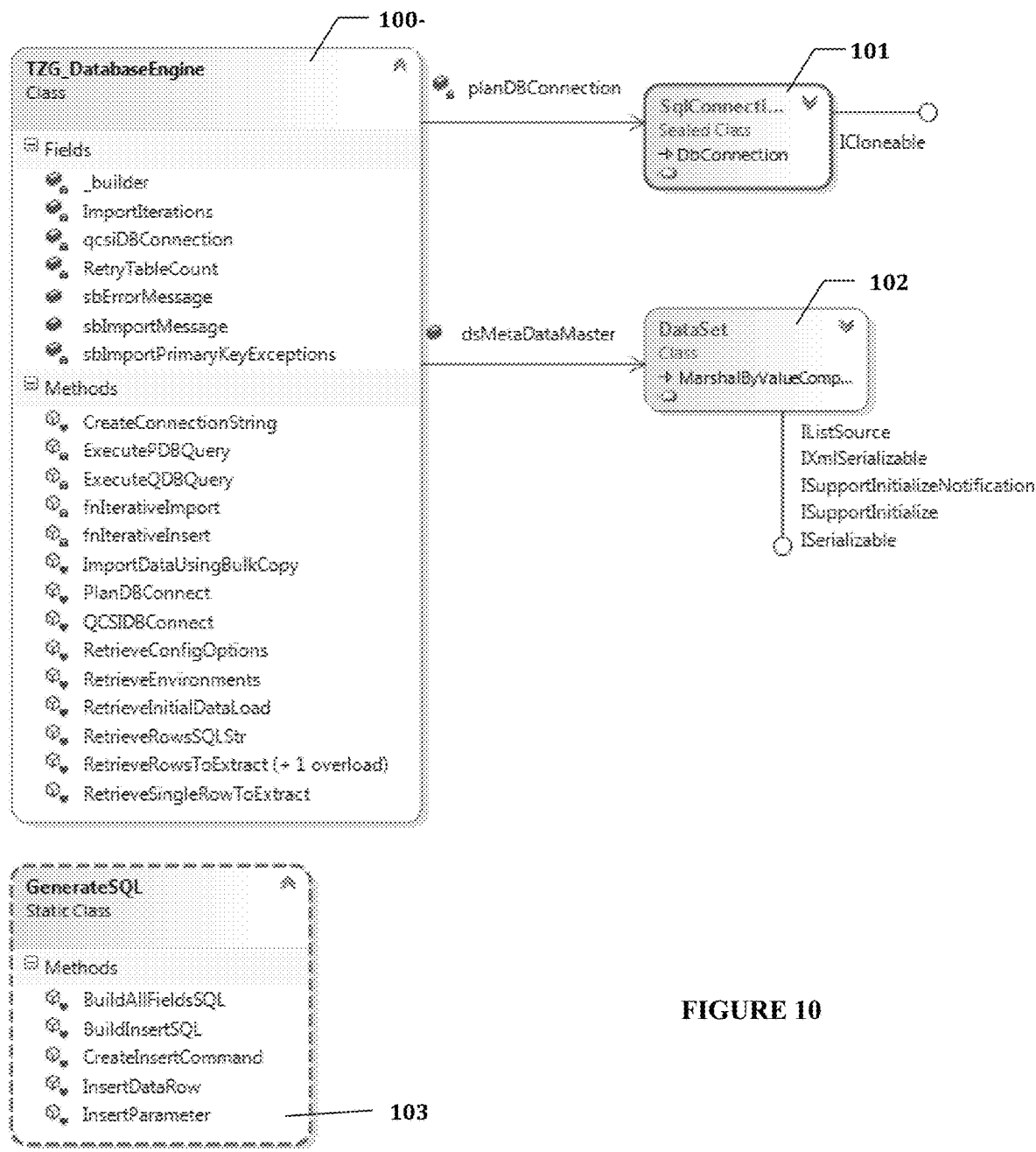
FIG. 10 depicts a claim diagram for an individual layer, namely the data layer.
Figure 12:
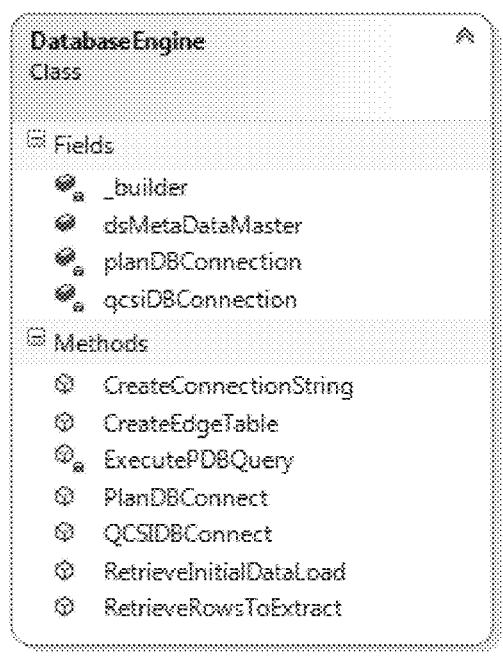
FIG. 12 provides another example of a claim diagram for an individual layer, namely the data layer.

FIG. 10 depicts the DatabaseEngine class 100 in the data layer, including the specifics fields and methods of that class. The SQL connections 101 and DataSet class 102 are also shown. An alternative to the DatabaseEngine class used with the process described above is shown in FIG. 12. The GenerateSQL static class, including identified methods, is shown as 103 in FIG. 10.

Figure 11:
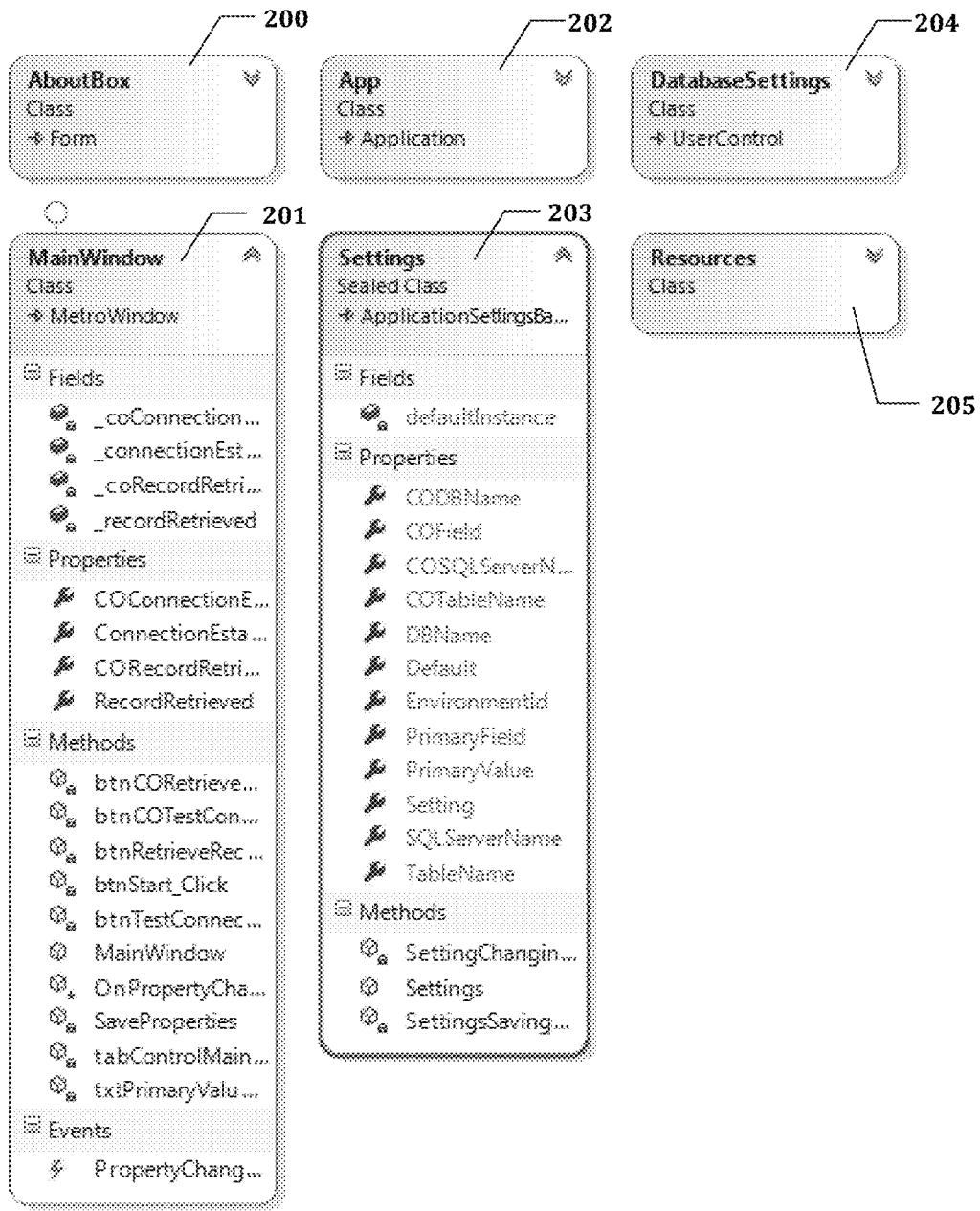
FIG. 11 depicts a claim diagram for an individual layer, namely the UI layer.

FIG. 11 sets forth classes in the User Interface (UI) layer. This UI layer includes an AboutBox class 200, MainWindow class 201, App class 202, and Settings sealed class 203. The DatabaseSettings 204 and Resources class 205 are also shown. The classes' fields, properties, and methods, respectively, are detailed.

The exemplary process, methods and acts described in the implementations presented previously are illustrative, and, in alternative implementations, certain acts can be performed in a different order, in parallel with one another, omitted entirely, and/or combined between different exemplary implementations, and/or certain additional acts can be performed without departing from the scope and spirit of the disclosure. Accordingly, such alternative implementations are included in the disclosures described herein.

The exemplary implementations can be used with computer hardware and software that perform the process, methods, and processing functions described above. Exemplary computer hardware include smart phones, tablet computers, notebooks, notepad devices, personal computers, personal digital assistances, and any computing device with a processor and memory area. As will be appreciated by those having ordinary skill in that art, the systems, methods, and procedures described herein can be embodied in a programmable computer, computer executable software, or digital circuitry. The software can be stored on computer readable media. For example, "computer code," "software application," "software module," "scripts," and "computer software code" are software codes or computer programs for the purposes of this disclosure. Further, "memory product," "memory," "computer-readable code product" are all storage and can include such media as floppy disk, RAM, ROM, hard disk, removable media, flash memory, memory stick, optical media, magneto-optical media, CD-ROM, etc.

Although specific implementations have been described above in detail, the description is merely for purposes of illustration. It should be appreciated, therefore, that many aspects described above are not intended as required or essential elements unless explicitly stated otherwise. Various modifications of, and equivalent acts corresponding to, the disclosed aspects of the exemplary implementations, in addition to those described above, can be made by a person of ordinary skill in the art, having the benefit of the present disclosure, without departing from the spirit and scope of the disclosure defined in the following claims, the scope of which is to be accorded the broadest interpretation so as to encompass such modifications and equivalent structures.

The invention claimed is:

1. A method for providing software support involving a software support issue with an entity comprising:
   recreating a software-generated scenario which resulted in the issue, the recreation including:
      exporting by a processor, data and relationships related to the entity from a first database to assist in resolving a software support issue, including debugging computer program code executing on one or more portions of the data involving one or more aspects related to the entity, wherein the entity is one of multiple entities stored in the first database;
      executing by the processor a sequence of function calls to collect data relevant to the one or more aspects related to said entity to export, wherein the data is stored across multiple data tables on the first database;
      executing by the processor a sequence of function calls to collect relationships relevant to the one or more aspects related to said entity to export, wherein collecting data and relationships includes identifying at least one parent key and at least one foreign key within the multiple data tables on the first database relevant to the one or more aspects related to said entity and tracking the at least one parent key and the at least one foreign key through the multiple data tables on the first database;
      creating a new data structure containing said collected entity, data, and relationships, wherein the new data structure is available for import by an analyst to provide the software support including debugging computer program code executing on one or more portions of the data;
      selecting to import the identified entity, data and relationships by the analyst and storing said data structure in a second database in association with the software support issue to facilitate the recreation of the software-generated scenario and the resolution of the software support issue, including debugging computer code executing on one or more portions of the data used in the recreation of the software-generated scenario.

2. The method in claim 1, wherein the entity is a healthcare claim.

3. The method in claim 1, wherein the entity is a healthcare member.

4. The method in claim 1, wherein the entity is a healthcare provider.

5. The method in claim 1, further comprising identifying a location of a database server upon which the entity and relevant data and relationships are stored in the first database.

6. The method in claim 1, further comprising storing the new data structure in an Extensible Markup Language format.

7. The method in claim 1, further comprising identifying at least one parent table and at least one child table of the entity.

8. A computer program for providing software support involving a software support issue with an entity comprising:
   a set of computer code for recreating a software-generated scenario which resulted in the issue, the set of computer code including:
      first computer code for exporting by a processor, data and relationships related to the entity from a first database to assist in resolving a software support issue, including debugging computer program code executing on one or more portions of the data involving one or more aspects related to the entity, wherein the entity is one of multiple entities stored in the first database;
      second computer code for executing by the processor a sequence of function calls to collect data relevant to the one or more aspects related to said entity to export, wherein the data and relationships related to the entity is stored across multiple data tables on the first database;
      third computer code for executing by the processor a sequence of function calls to collect relationships relevant to the one or more aspects related to said entity to export, wherein collecting data and relationships includes identifying at least one parent key and at least one foreign key within the multiple data tables on the first database relevant to the one or more aspects related to said entity and tracking the at least one parent key and the at least one foreign key through the multiple data tables on the first database;
      fourth computer code for creating a new data structure containing said collected entity, data, and relationships wherein the new data structure is available for import by an analyst to provide the software support including debugging computer program code executing on one or more portions of the data; and
      fifth computer code for selecting to import the identified entity, data and relationships by an analyst and storing said data structure in a second database in association with the software support issue to facilitate a recreation of the software-generated scenario and the resolution of the software support issue, including debugging computer code executing on one or more portions of the data used in the recreation of the software-generated scenario.

9. The computer program in claim 8, wherein the entity is a healthcare claim.

10. The computer program in claim 8, wherein the entity is a healthcare member.

11. The computer program in claim 8, wherein the entity is a healthcare provider.

12. The computer program in claim 8, further comprising identifying a location of a database server upon which the entity and relevant data and relationships are stored in the first database.

13. The computer program in claim 8 further comprising storing the new data structure in an Extensible Markup Language format.

14. The computer program in claim 8, further comprising identifying by the second computer code at least one parent table and at least one child table of the entity.

15. A method for providing software support involving a software support issue with an entity comprising:
   recreating a software-generated scenario which resulted in the issue, the recreation including:
      importing by a processor, data and relationships related to the entity from a first database to assist in resolving a software support issue, including debugging computer program code executing on one or more portions of the data involving one or more aspects related to the entity, wherein the entity is one of multiple entities stored in the first database;
      wherein said importing includes importing a data structure identifying said entity and data and relationships relevant to the one or more aspects related to said entity to enhance the resolution of the software support issue, wherein the data is stored across multiple data tables on the first database and further wherein identifying data and relationships includes identifying at least one parent key and at least one foreign key within the multiple data tables on the first database relevant to the one or more aspects related to said entity and tracking the at least one parent key and the at least one foreign key through the multiple data tables on the first database;
      creating an Extensible Markup Language (XML) data structure containing said identified entity, data, and relationships, wherein the XML data structure is available to provide the software support including debugging computer program code executing on one or more portions of the data; and
      storing the XML data structure in a second database in association with the software support issue to facilitate the recreation of the software-generated scenario and the resolution of the software support issue by an analyst, including debugging computer code executing on one or more portions of the data used in the recreation of the software-generated scenario.

16. The method in claim 15, wherein the entity is a healthcare claim.

17. The method in claim 15, wherein the entity is a healthcare member.

18. The method in claim 15, wherein the entity is a healthcare provider.

* * * * *